(12) United States Patent
Hakky et al.

(10) Patent No.: US 8,137,337 B2
(45) Date of Patent: Mar. 20, 2012

(54) INDWELLING URINARY CATHETER WITH SELF-RETAINING MECHANISM

(76) Inventors: Said I. Hakky, Largo, FL (US); A-Hamid Hakki, Dunedin, FL (US)

( * ) Notice: Subject to any disclaimer, the term of this patent is extended or adjusted under 35 U.S.C. 154(b) by 49 days.

(21) Appl. No.: 12/490,669

(22) Filed: Jun. 24, 2009

(65) Prior Publication Data
US 2010/0331825 A1    Dec. 30, 2010

(51) Int. Cl.
    *A61M 29/00* (2006.01)
(52) U.S. Cl. .................... 604/544; 604/104
(58) Field of Classification Search ............ 604/544, 604/6.16, 19, 93.01, 103.03, 104, 105, 107, 604/164.01, 174, 264, 540, 541, 543; 600/29–31, 600/38–41; 128/885, 897–898; 606/201–202
See application file for complete search history.

(56) References Cited

U.S. PATENT DOCUMENTS

| | | | |
|---|---|---|---|
| 1,870,942 A * | 8/1932 | Beatty | 604/58 |
| 3,713,447 A * | 1/1973 | Adair | 604/105 |
| 3,946,741 A * | 3/1976 | Adair | 604/105 |
| 4,154,242 A * | 5/1979 | Termanini | 604/105 |
| 5,707,357 A | 1/1998 | Mikhail et al. | |
| 5,882,340 A * | 3/1999 | Yoon | 604/164.12 |
| 5,976,068 A * | 11/1999 | Hakky et al. | 600/29 |
| 6,632,197 B2 * | 10/2003 | Lyon | 604/107 |
| 7,104,981 B2 * | 9/2006 | Elkins et al. | 604/528 |
| 7,306,586 B2 | 12/2007 | Beaufore et al. | |
| 2008/0172042 A1 | 7/2008 | House | |
| 2008/0228175 A1 * | 9/2008 | Snell et al. | 604/544 |
| 2009/0299261 A1 * | 12/2009 | Bognar | 604/6.16 |

FOREIGN PATENT DOCUMENTS

EP   1023882 A1   8/2000

OTHER PUBLICATIONS

International Search Report of PCT/US2009/050544 dated Aug. 24, 2010.

* cited by examiner

*Primary Examiner* — Tatyana Zalukaeva
*Assistant Examiner* — Benedict L Hanrahan
(74) *Attorney, Agent, or Firm* — Rosenberg, Klein & Lee

(57) ABSTRACT

A urinary catheter with an improved retaining and activating feature is provided which is a safe device with reduced irritation and discomfort to a patient. The retaining mechanism positioned at the proximal end of the catheter assumes a "close" state for introduction and removal of the catheter into and from the urethral tract, and is transitioned into the "open" state when the catheter is in the bladder by mechanically manipulating the retaining mechanism through the activation mechanism. An actuating linkage wire connected between the retaining mechanism and activation mechanism controllably reciprocates in the channel of the catheter to transition the catheter between the "open" and "closed" states.

10 Claims, 13 Drawing Sheets

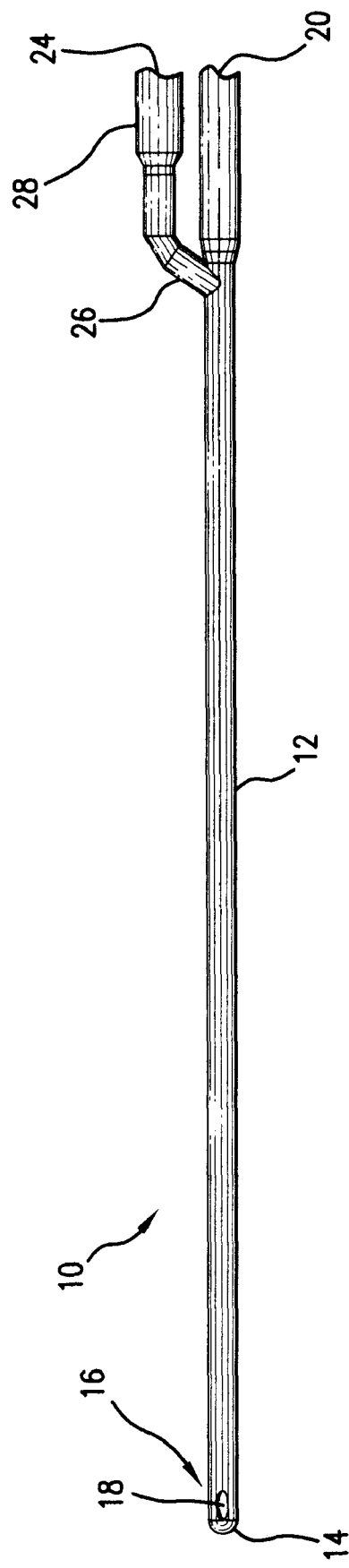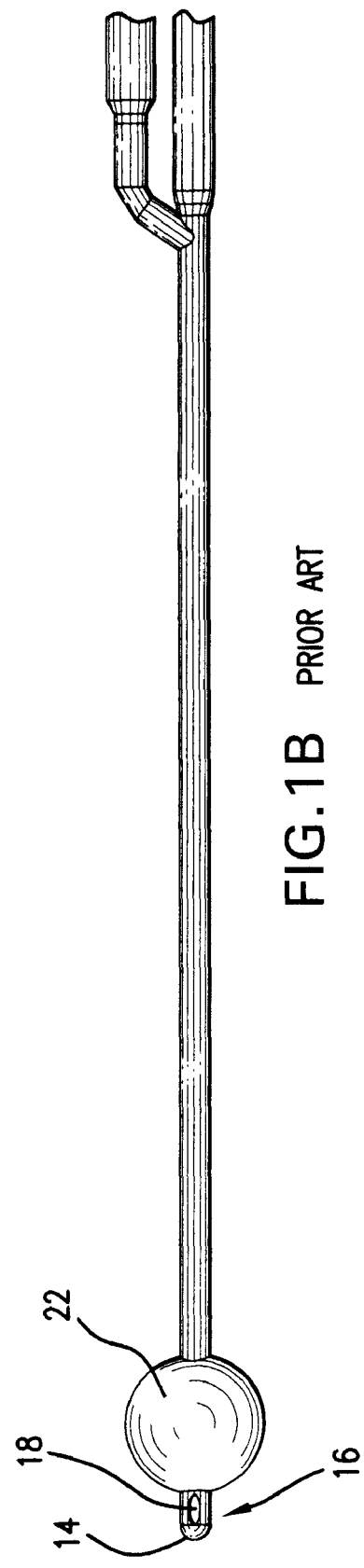
FIG. 1A PRIOR ART
FIG. 1B PRIOR ART

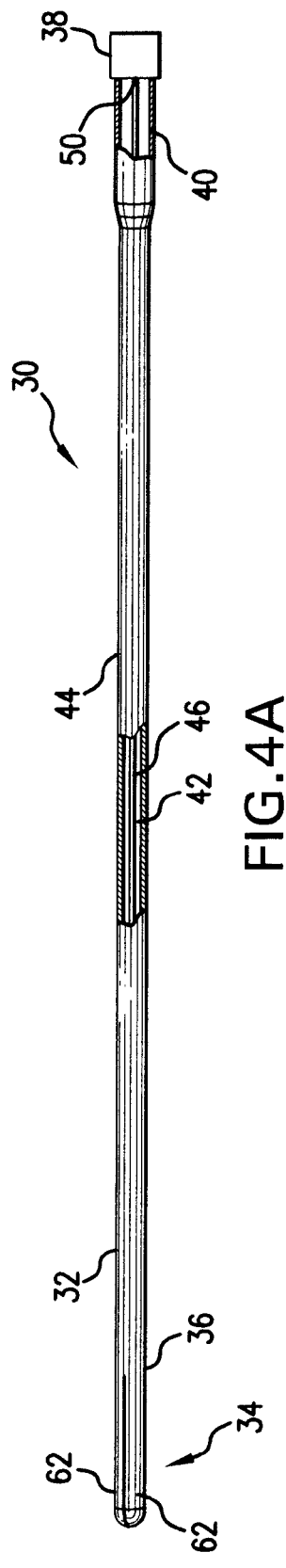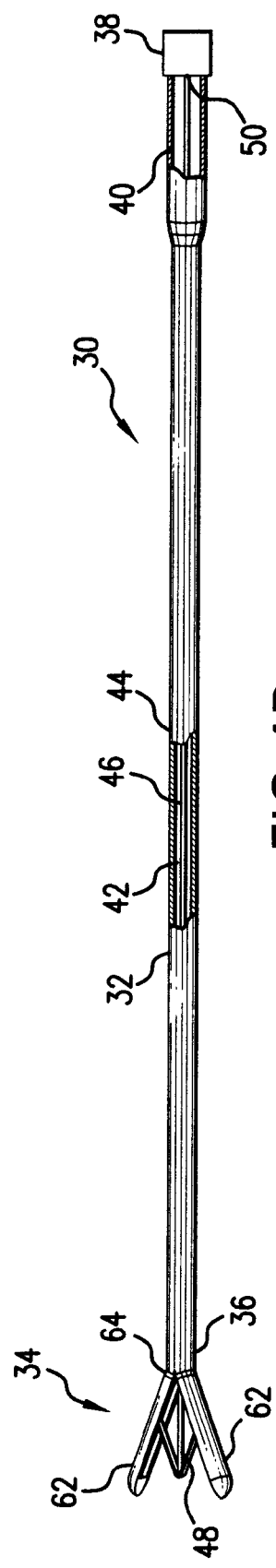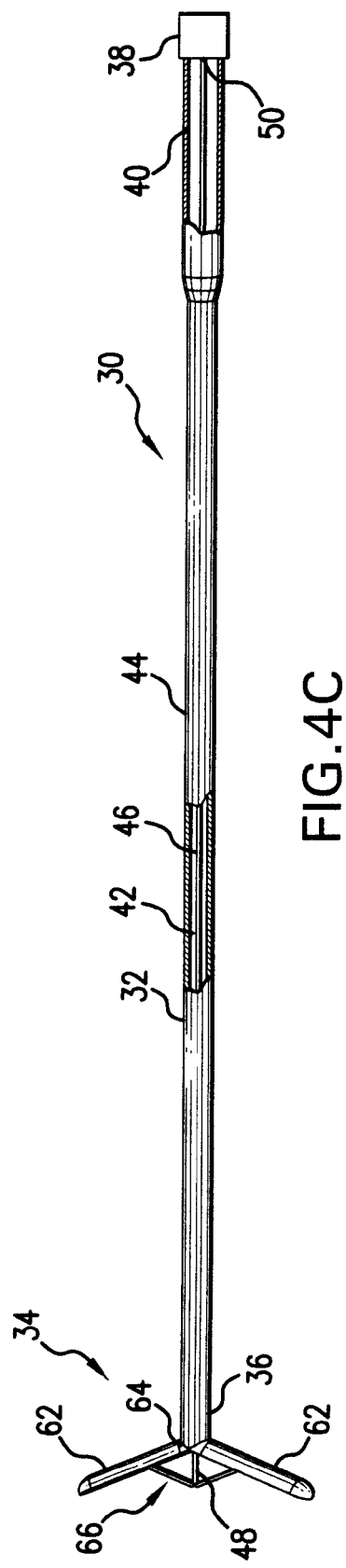

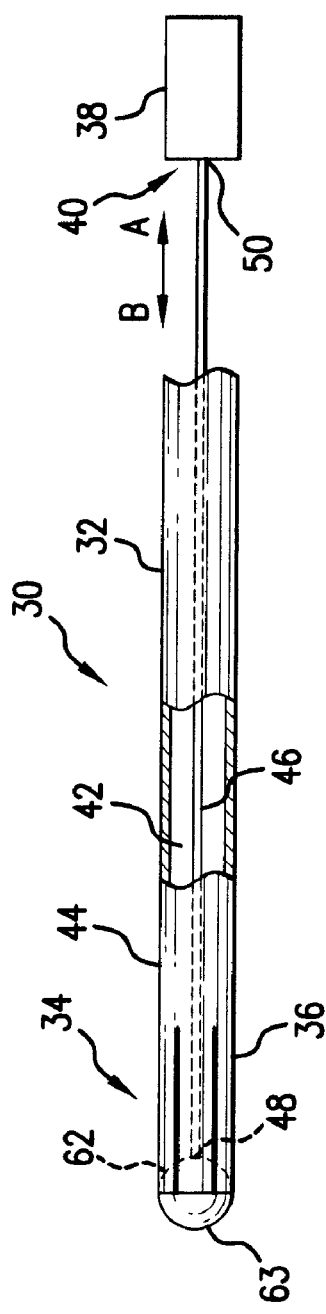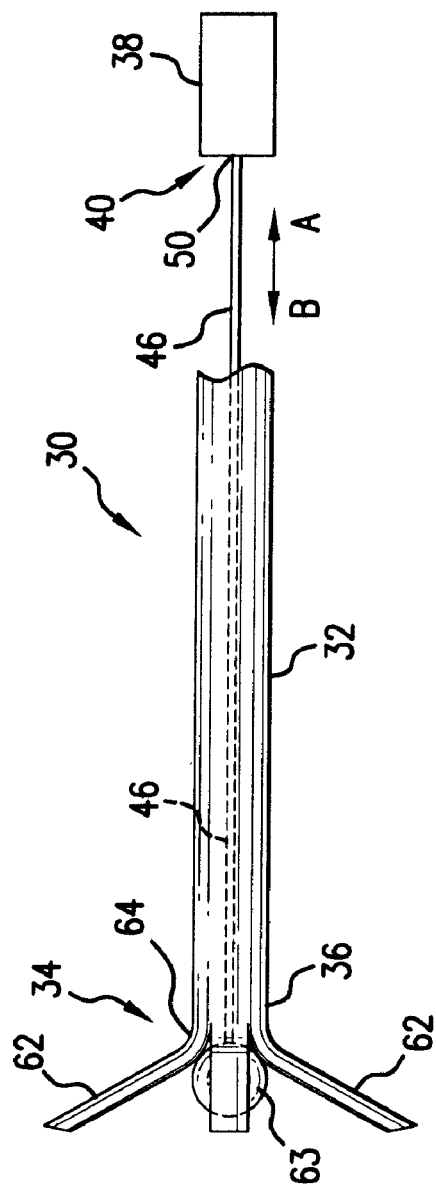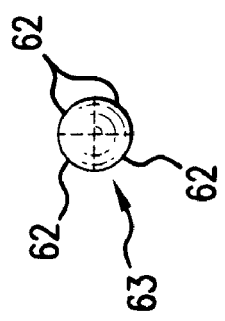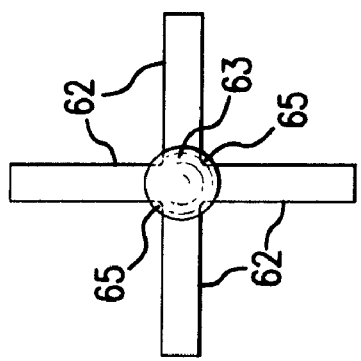

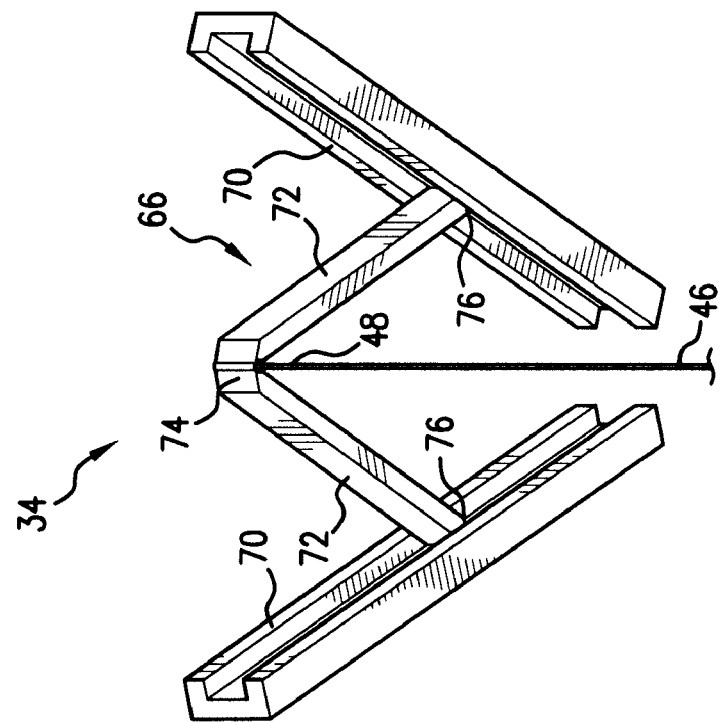
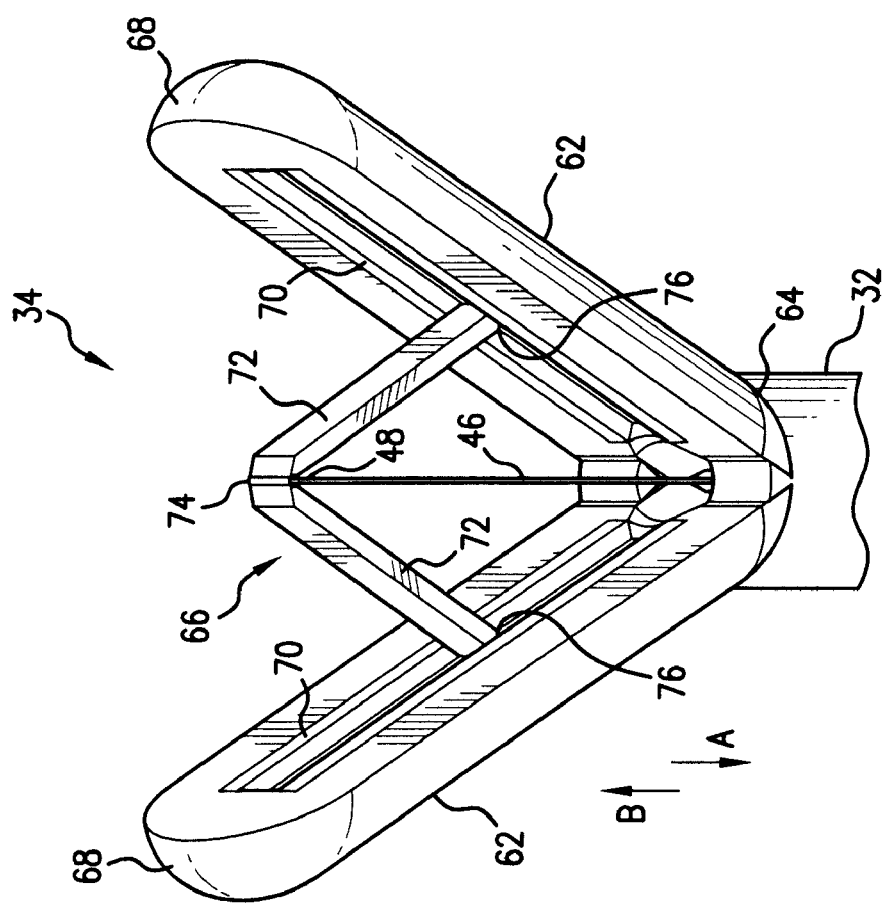

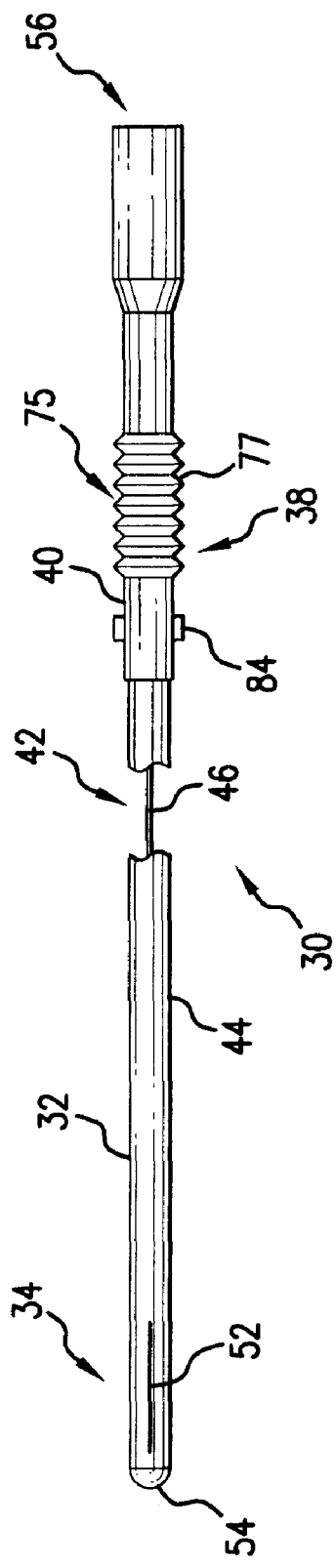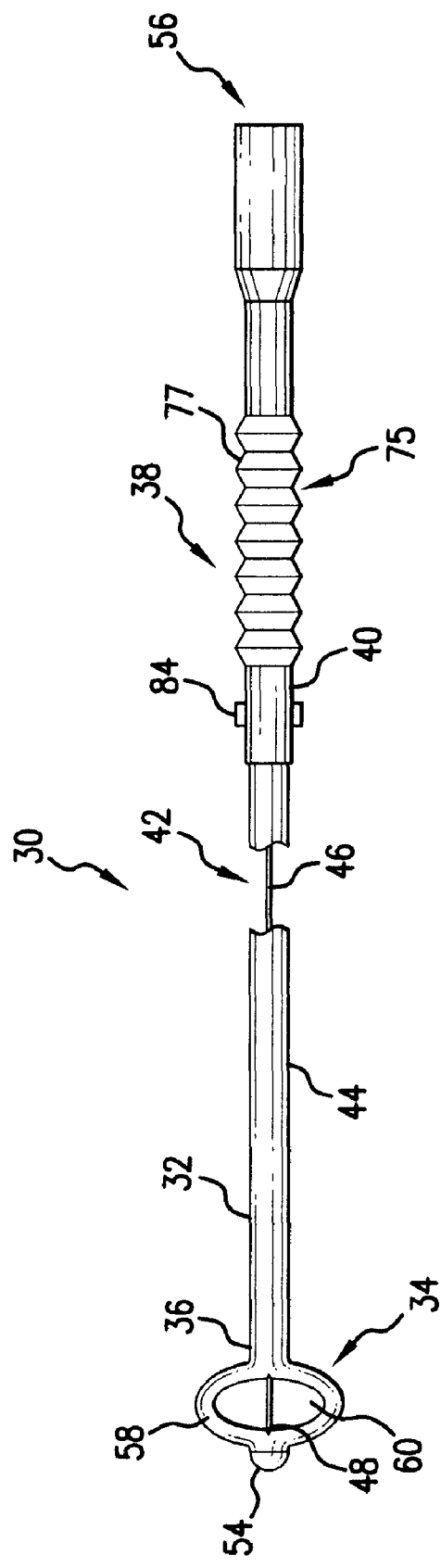

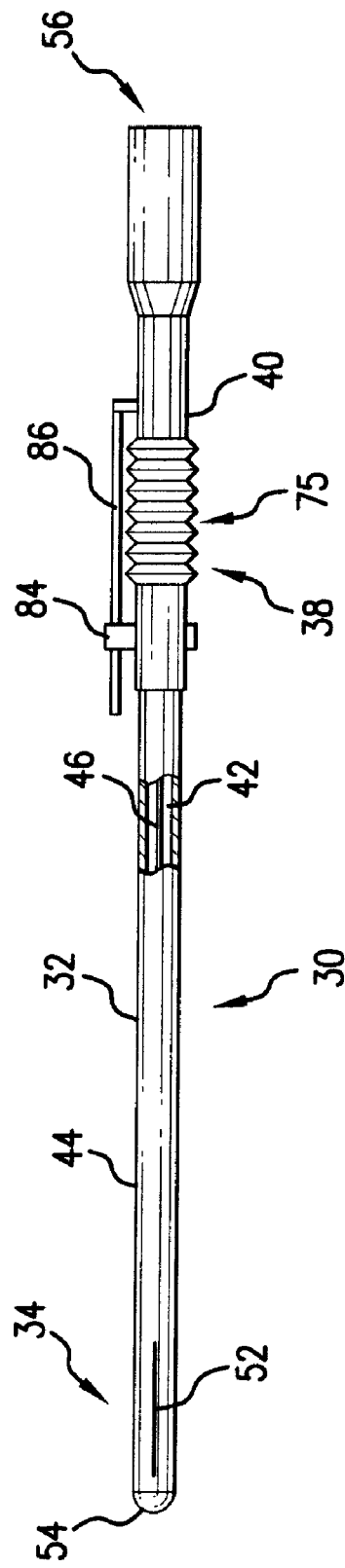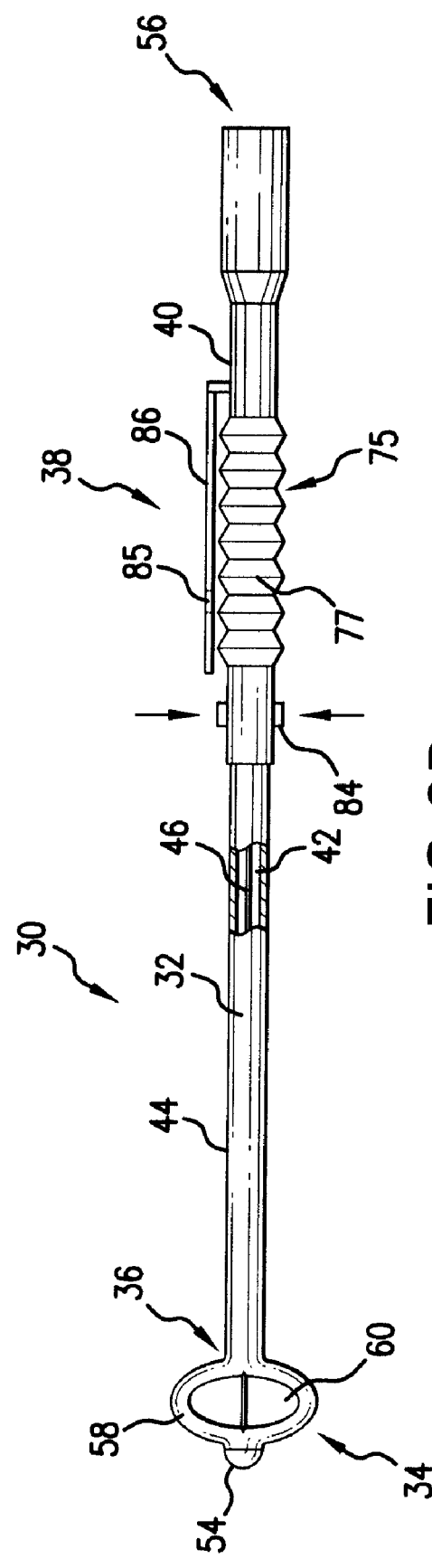

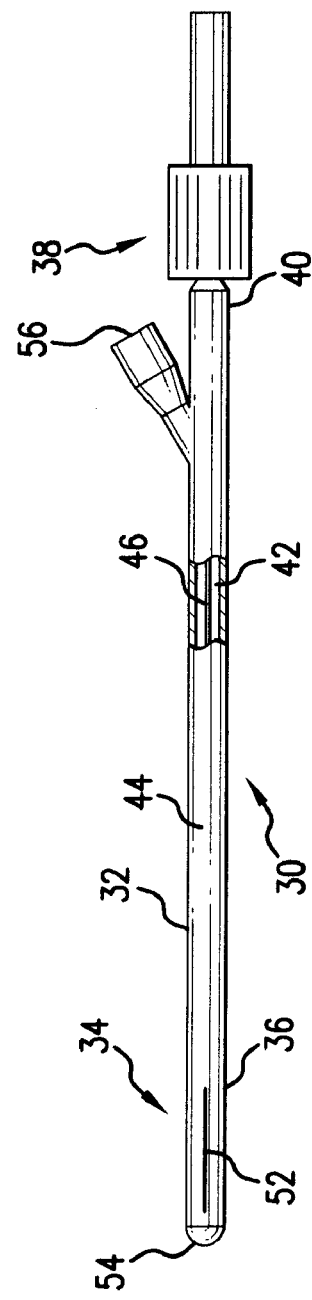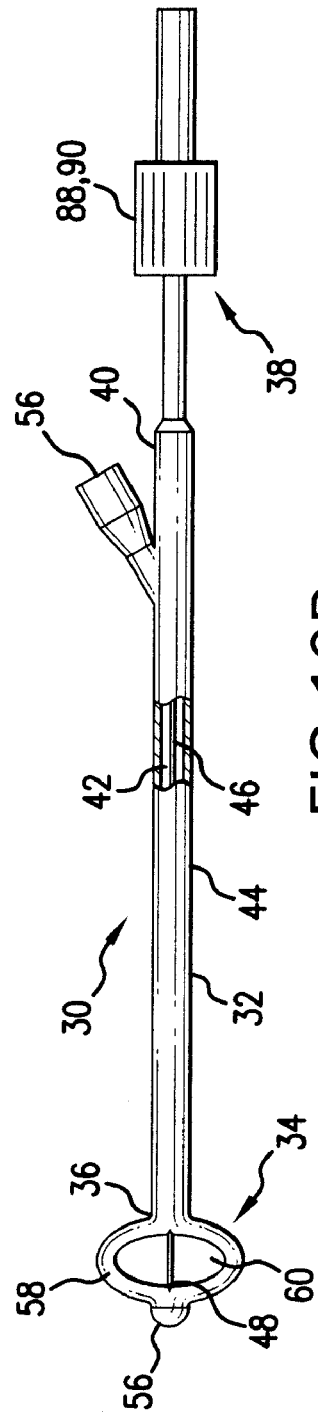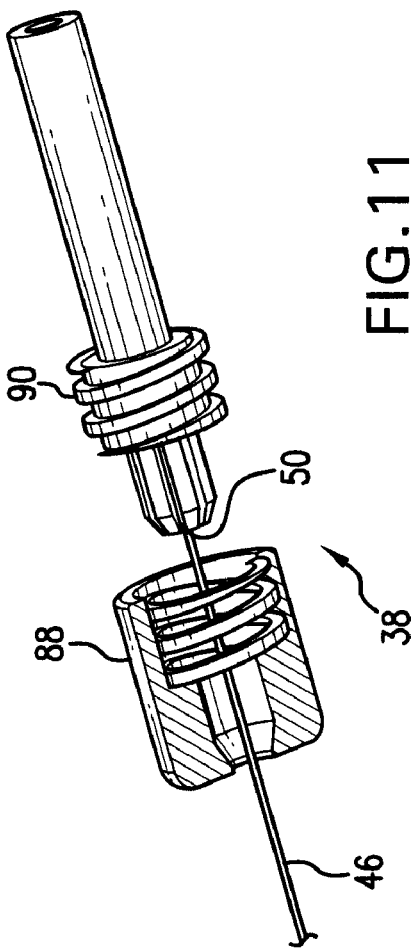

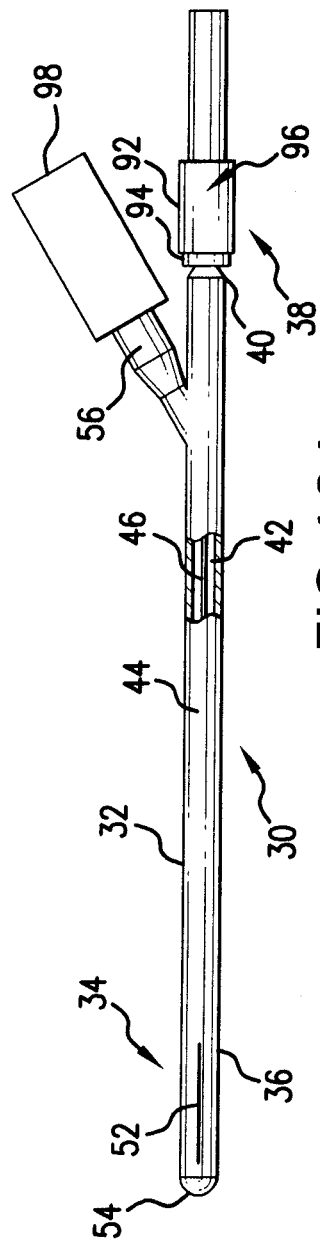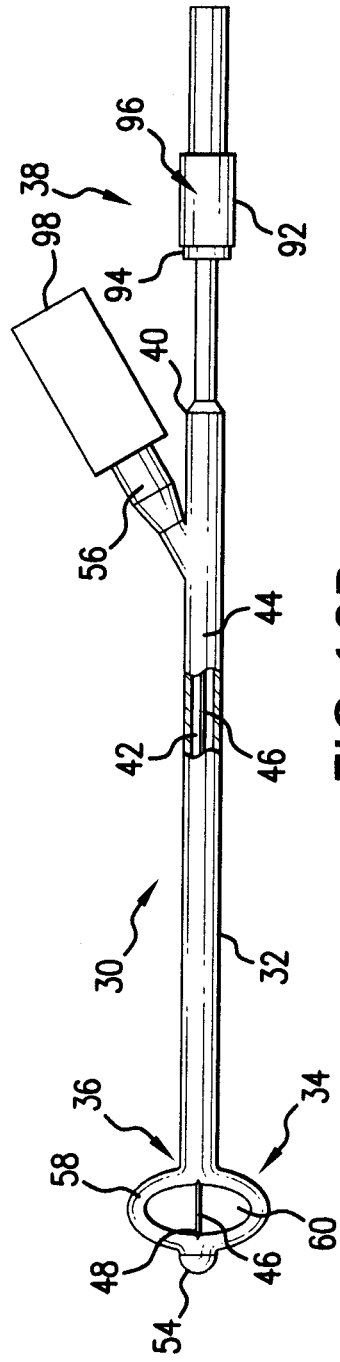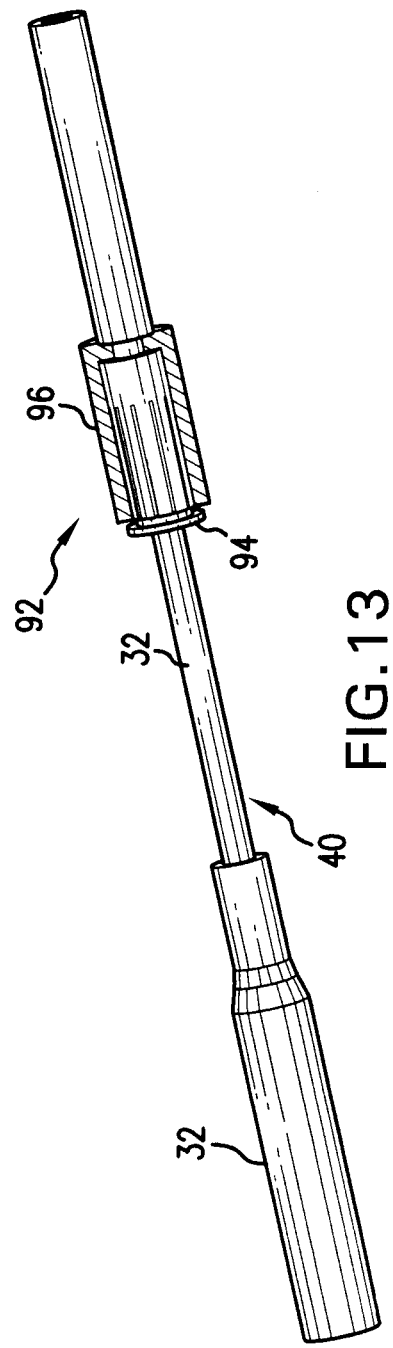

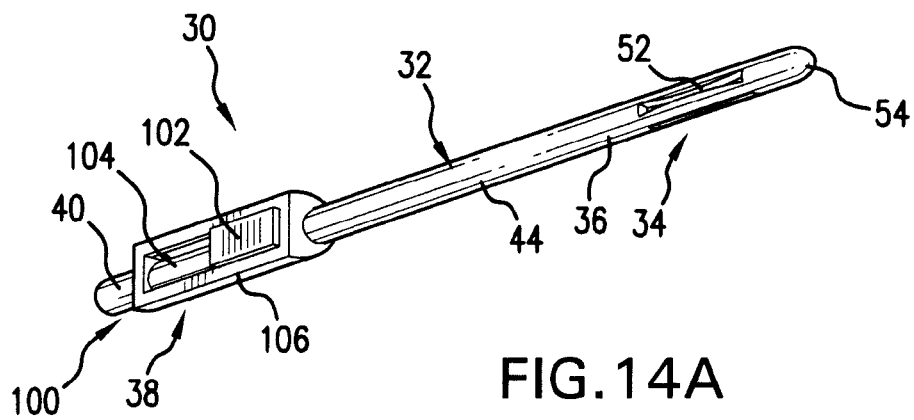
FIG.14A
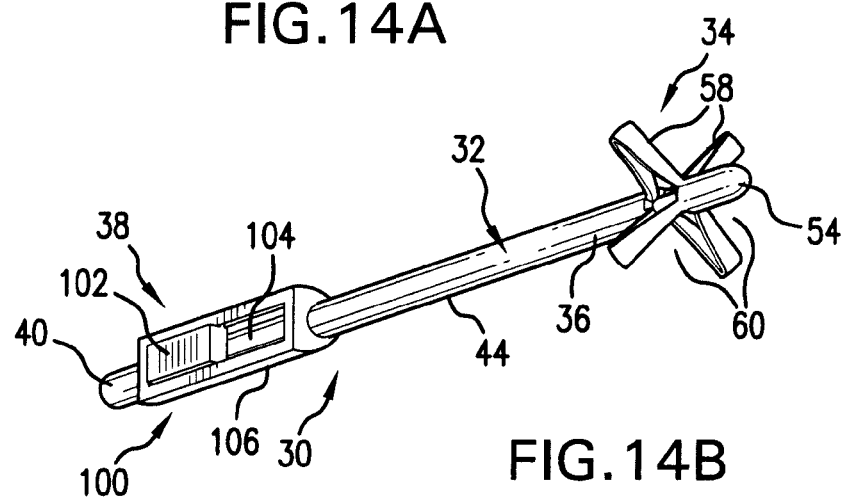
FIG.14B
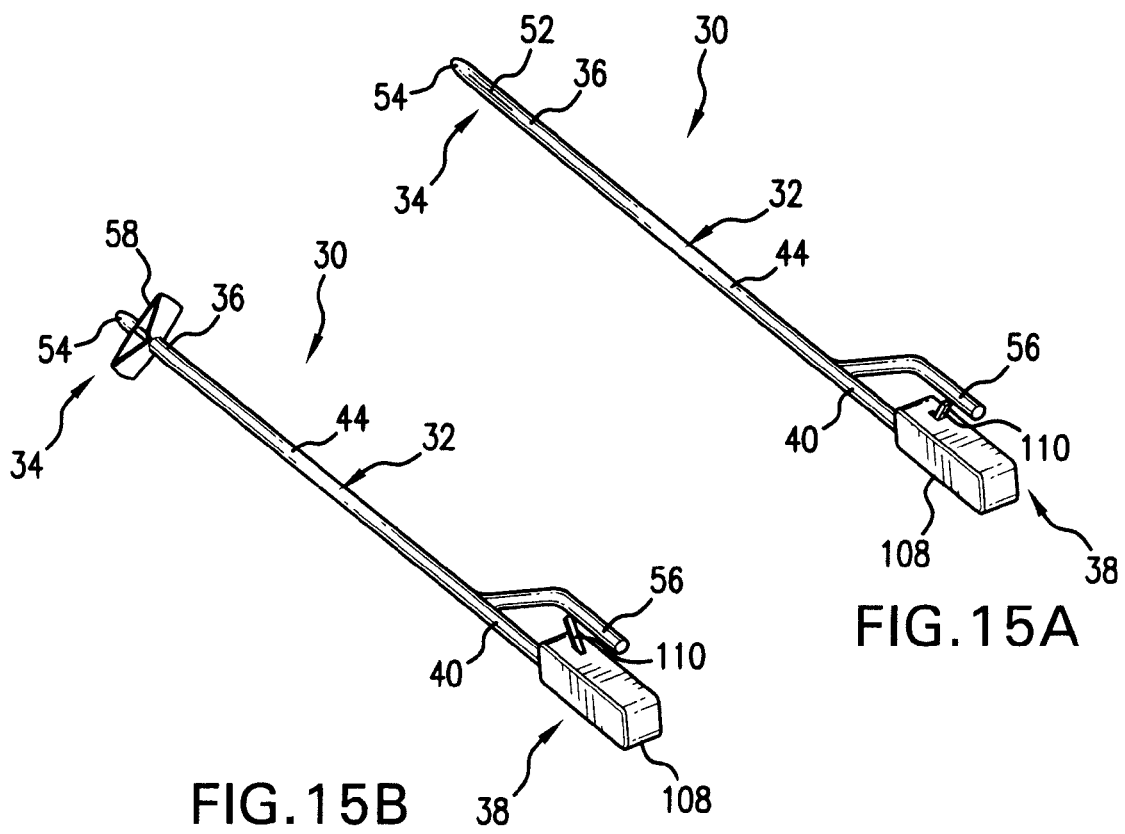
FIG.15A
FIG.15B

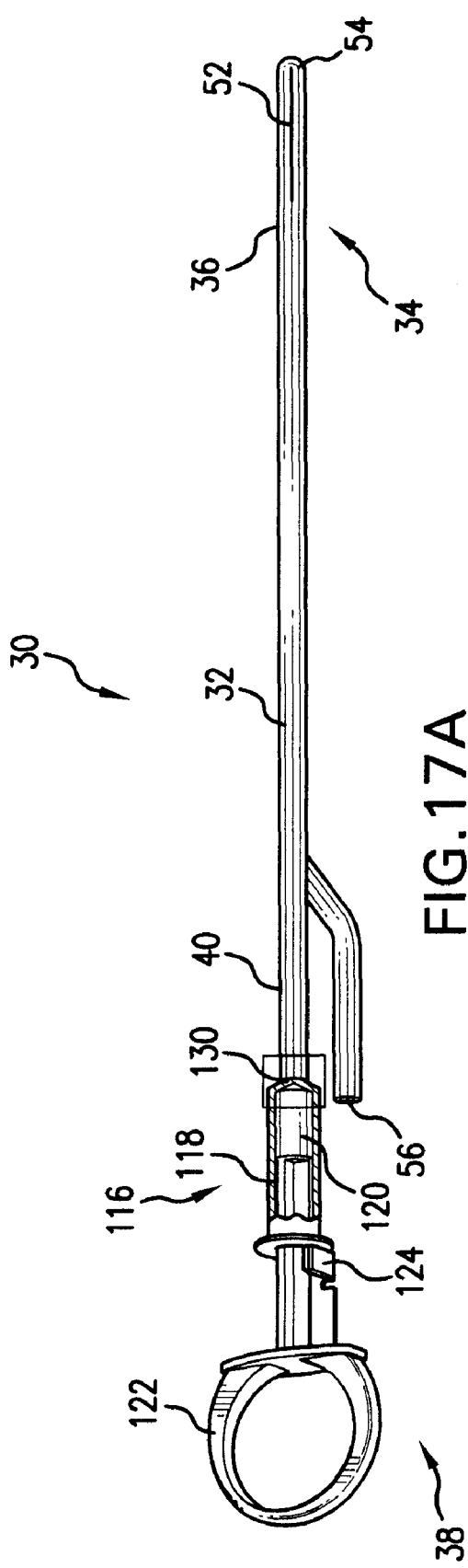
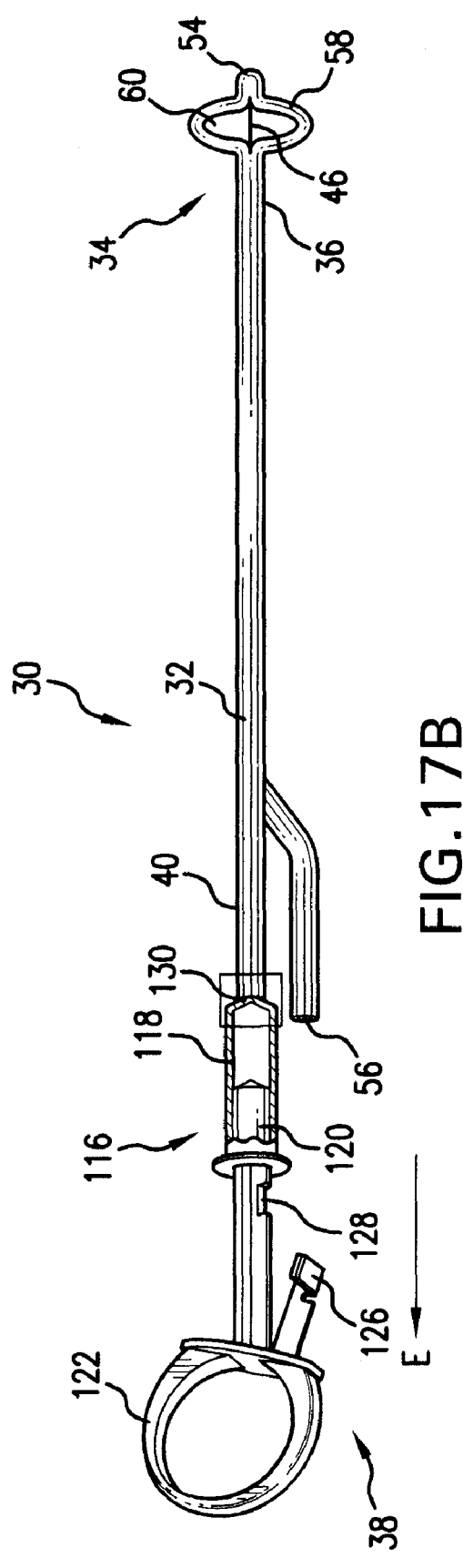

US 8,137,337 B2

INDWELLING URINARY CATHETER WITH SELF-RETAINING MECHANISM

FIELD OF THE INVENTION

The present invention relates to surgical devices, and more in particular to catheters indwelled in the bladder of a patient for drainage, irrigation, or medicine delivery.

More in particular, the present invention is related to indwelling urinary catheters with self-retaining properties which are safe and reliable in operation, easily manipulatable, and leave no residual urine.

BACKGROUND OF THE INVENTION

Indwelling catheters are urinary catheters which are designed to be inserted into the bladder of a patient to remain therein for the duration of certain surgical procedures or longer. In acute and chronic surgical and medical conditions, it is desirable to continuously drain the urinary bladder to irrigate the bladder, or to deliver a medicine. For example, it may be desirable to drain the urinary bladder to measure the hourly urinary output which is an important parameter for calculation of the response of the patient to certain medications such as for example, diuretics. The hourly urinary output is also an important indicator of the kidney function in the study of the pulse rate, fluctuations in the blood pressure, and in cardiac monitoring. In comatose patients, the urinary drainage is important as a part of the total assessment of the patient's medical condition.

Thorough drainage of the bladder has been known to expedite the recovery in spinal cord injuries. Additionally, indwelling urinary catheters are indicated for patients suffering from complicated neurological diseases or who may be heavily sedated and unable to empty their bladder.

In prostate surgery, post-operative bleeding is common, and if left unchecked, may lead to formation of blood clots in the bladder. Indwelling urinary catheters are mandatory to ensure the bladder is not filled with clotting blood and to avoid painful conditions, or shock associated with unrecognized clotting of the bladder.

In certain post prostate or bladder surgeries, the urinary bladder should be continuously irrigated with fluid to prevent blood from clotting inside the urinary bladder. Continuous bladder irrigation is achieved using three-way catheters having an inlet for fluid injection and a drainage tube. If delivery of medication to the urinary bladder is needed on a continuous basis, then the urinary catheter is indwelled and remains in the bladder for the entire duration of the treatment.

In chronic medical and surgical conditions, the urinary bladder may have to be drained for weeks, months, or in some cases for life. Examples of such conditions include debilitated patients unable to urinate and when the patient's medical condition prohibits surgical intervention.

A common type of indwelling catheter, known as a Foley catheter, has a balloon attachment at one end. After the Foley catheter is inserted into the urinary tract and arrives in the bladder, the balloon is filled with sterile water so that the filled balloon prevents the catheter from escaping the bladder. Specifically, as presented in FIGS. 1A and 1B, the Foley catheter 10 has a tubular body 12 with a tip 14 at a proximal end 16. Adjacent to the tip 14, there are several holes or openings 18 (usually with 3×5 mm dimensions) for urinary or blood drainage or medication delivery when the catheter is inserted into the bladder.

In the urinary procedure, the catheter in its closed state, shown in FIG. 1A, is inserted through the urinary tract into the bladder, and the urine and/or blood contained in the bladder penetrates through the holes 18 into the channel within the tubular body 12 to be discharged at the main drainage outlet 20. In order to provide retention of the catheter within the bladder, a sterile fluid is delivered to the balloon 22 by a syringe coupled to the injection port 24. The injection port 24 is connected to the balloon 22 through a separate channel 26 extending along the tubular body 12 of the catheter 10. The main drainage outlet 20 is usually connected to a large urine bag (not shown). A valve 28 is provided at the injection port 24 to facilitate the injection of the sterile fluid when the catheter is to be indwelled.

In the indwelling position, shown in FIG. 1B, with the balloon 22 inflated, the catheter remains in the bladder until it is to be removed. For the removal of the catheter from the bladder, the sterile fluid is removed from the balloon 22 by means of the syringe engaged with the injection port 24 through the valve 28. Once the balloon is deflated, and the catheter is transitioned into the "balloon deflated" state, the catheter may be removed.

The urinary Foley catheter has several disadvantages:

1. The balloon near the tip, when filled with water, may weigh 5-50 grams, depending on how many cubic centimeters of water is injected into the balloon. The balloon with such significant weight "sits" on the most sensitive part of the bladder, e.g., the trigone, thus producing discomfort, irritation and pain. The catheter balloon also prevents complete drainage of urine so that there is residual urine in the bladder at all times. This may cause irritation and eventually initiate infection of the bladder.

2. Accidental inflation of balloon inside the urethra (before arriving in the bladder) is an undesirable situation which may cause urethra injury and even partial urethra tear. Partial or complete urethra tear may produce narrowing of the urethra, known as "urethral stricture", which may need a complicated surgical procedure to rectify the stricture.

In some cases, the balloon may fail to deflate when the catheter is to be removed. The patient in this situation must be subjected to a complicated procedure in order to puncture the balloon inside the urinary bladder.

3. Accidental pulling of the catheter while the balloon is inflated inside the bladder may occur. This is very painful and may lead to the injury of the bladder neck and/or urethra.

4. In order to leave the catheter indwelling, a sterile syringe and a sterile fluid are needed to inflate the balloon. To the contrary, if the catheter is to be removed from the bladder, a sterile syringe is used to withdraw the fluid from the balloon in order to deflate the balloon. The use of the sterile syringe and fluid transfer complicates the procedure.

A catheter called "Comficath" has been developed which is coated with antibiotics, or Silicon. In some catheters, the issue of Latex®, as a source of irritation, has been addressed, and a new generation of rubber Silicon catheters has been developed. In spite of all these innovations, the problems persist, and a catheter free of the above-presented shortcomings associated with the Foley catheter, namely, presence of residual urine, infection, discomfort, malfunctioning and accidental possible injury to the urethra and/or bladder neck, is still needed in the medical field.

Therefore, it is desirable to provide a urinary catheter with an improved retaining mechanism which is free of the problems associated with the inflating/deflating of the balloon wherein there is a long lasting need in the field of indwelling catheters to alleviate the above discussed anomalies.

SUMMARY OF THE INVENTION

It is an object of the present invention to provide an indwelling catheter with a retaining mechanism, the state of which is easily controlled by a person administering the urinary procedure and which is safe for the patient.

It is a further object of the present invention to provide an indwelling catheter for emptying the bladder in acute and chronic surgical and medical conditions, for bladder drainage, for irrigating the bladder with fluids or medications with minimized discomfort and irritation, with the added object of not leaving residual urine in the bladder.

It is a further object of the present invention to provide an indwelling catheter with an improved retaining mechanism at the proximal end which is easily actuated by a person administering the procedure with no need of a sterile syringe or a sterile fluid and which is sufficiently stiff for introduction inside urinary bladder without the need for a stylet or a catheter introducer.

The urinary catheter of the present invention includes a tubular member defining a longitudinal channel extending between the proximal and distal ends thereof. A retaining mechanism is located at the proximal end of the tubular member for insertion into the urinary tract of a patient. An activation mechanism is positioned at the distal end of the tubular member. An actuation linkage extends in the longitudinal channel of the tubular member of the catheter and is operatively coupled to the retaining and activation mechanisms in order to actuate the retaining mechanism to assume either an "open" state in which the catheter is retained in the bladder or a "closed" state used for insertion and removal of the catheter.

The actuation linkage is formed as a stainless steel wire, nylon wire, Dacron wire, or a plastic wire, etc., and reciprocates within the longitudinal channel of the tubular member of the catheter under the control of the activation mechanism. When the actuation linkage wire is retracted towards the distal end, the retaining mechanism is transformed into the "open" state, and when the actuation linkage wire is moved towards the proximal end, the retaining mechanism is transitioned in the "closed" state.

In addition to the distal port at the distal end of the tubular member to which the activation mechanism is operatively attached, the catheter also includes a drainage outlet coupled to the tubular member in fluid communication with the longitudinal channel for drainage of fluids from the urinary tract of the patient, or for delivery of medication or irrigation fluids to the bladder. In the three-way catheter design, an extra port is added to the wall of the catheter for continuously injecting medications or irrigating fluids.

There are several modifications of the retaining mechanism contemplated in the present urinary catheter. For example, the retaining mechanism may include a pair of slits extending from a tip of the catheter along the wall of the tubular member, which are transformable into "wings" extending radially from the walls of the tubular member and spanning a distance corresponding to the length of the slits formed in the walls of the tubular member at the proximal end thereof.

When inserted into the bladder in the "closed" state, the catheter is transformed into the "open" state and the wings hold the catheter inside the bladder touching against the walls of the bladder. The flexible material (silicone rubber or Latex) of the tubular member makes the thus created wings of the retaining mechanism "user friendly" causing minimal irritation to the walls of the bladder by contact with the wings. Additionally, the openings formed between the wings are quite large to permit a full drainage of the fluid from the bladder and effective delivery of medication or irrigation fluid to the bladder when needed.

In an alternative embodiment, the retaining mechanism may include a pair or more of leaves coupled to the tubular member at the proximal end thereof. In the "closed" state of the retaining mechanism, the leaves are positioned in contact to each other along the entire length thereof and in alignment with a tubular member. In the "open" state of the retaining mechanism, the leaves are displaced a predetermined angle each from the other to form points of contact with the walls of the bladder at the ends to reliably hold the catheter in place.

The retaining mechanism with the leaves is enhanced with ∧-shaped memory block which "remembers" the shape. In the "open" state of the retaining mechanism, the ∧-shaped memory block is transitioned by the actuation linkage wire into the "deployed" state, in which the legs of the ∧-shaped memory block push the leaves of the retaining mechanism apart to form a predetermined angle therebetween.

In order to transform the retaining mechanism into the "closed" position, the ∧-shaped memory block is released from the "open" position by the actuation linkage, thus causing the closure of the leaves. The retaining mechanism remains in the "closed" state since the ∧-shaped memory block has a memory of the "closed" shape.

The activation mechanism of the subject catheter is contemplated in several embodiments, each of which is applicable to each of the above-described retaining mechanisms. In one of the embodiments, the activation mechanism includes a bellows member which has flexible corrugated walls. The front end of the actuation linkage is connected to the retaining mechanism, while a tail end of the actuation linkage is connected to the end of the bellows member most distant from the proximal end of the catheter. The bellows member may transition between its fully compressed state and the expanded state to actuate the "closed" or "open" states of the retaining mechanism, respectively.

The bellows member may be a memory block which may have a shape memory either of the expanded state, i.e., the compressed state, or both states, or neither. Depending on the choice of the shape memory of the bellows member, for example if the bellows member has a memory of the expanded state corresponding to the "open" state of the retaining mechanism, a latch may be used to hold the bellows member in the compressed state. When the catheter in its "closed" state is inserted into the bladder, the latch is released by medical personnel administering the procedures, thereby releasing the bellows member into the expanded state in which the bellows member remains due to the shape memory.

When the catheter needs to be removed from the bladder, the bellows member is compressed and closed by the latch. A pair of resiliently biased projections (buttons) may be installed at one of the ends of the bellows member in engagement with the latch, so that when the latch is to be released to transition the bellows member in the expanded state, both buttons are compressed for releasing the latch.

If the bellows member has a memory of the compressed shape, it may be manually expanded and "locked" in the expanded position by a locking mechanism, for example, a latch.

Alternatively, the activation mechanism may be envisioned as having a pair of threadedly engaging members. The tail end of the actuation linkage is connected to one of the threaded members so that the transformation between the "open" and "closed" states of the retaining mechanism is controlled by the extent of the threaded engagement between the first and second threaded members of the activating mechanism.

Further, the activation mechanism may include a squeezable unit attached to the distal end of the tubular member in encircling relationship therewith. By squeezing and pushing the squeezable unit along the tubular member of the catheter, the displacement of the squeezable unit along the tubular member may be controlled. The "open" and "closed" states of the subject catheter are controlled by displacing the squeezable unit with the tail end of the actuation linkage attached.

The activation mechanism, specifically the latch control of the bellows member, may be designed as a thumb slide based actuator or as a lever based mechanism.

As a further example of the activation mechanism, a syringe based actuator is contemplated which includes a hollow cylinder portion attached to the distal end of the tubular member and a plunger portion controllably sliding within the hollow cylinder portion. The tail end of the actuation linkage in this embodiment is connected to the plunger portion. The transformation between the "open" and "closed" states of the retaining mechanism is controlled by relocating the plunger portion within the hollow cylinder portion of the syringe based actuator. The syringe based actuator may include a locking mechanism for locking the retaining mechanism in the "open" state. The syringe based actuator also may include a sealing means preventing fluid escape from the distal end of the tubular member.

These and other features and advantages of the present invention will become apparent in view of the further detailed description if taken in conjunction with the accompanying Patent Drawings.

BRIEF DESCRIPTION OF THE DRAWINGS

FIGS. 1A-1B is a schematic representation of the Foley catheter of the prior art;

FIGS. 4A-4C is a schematic representation of an alternative embodiment of the catheter of the present invention with two leaves in the "closed" state of the retaining mechanism (FIG. 5A), in an "open" state (FIG. 4C), and in an intermediate state (FIG. 4B);

FIGS. 5A-5D is a schematic representation of a modification of the catheter of the present invention with a four leaves retaining mechanism;

FIGS. 6A-6B show the activation mechanism of the catheter presented in FIGS. 4A-4C on a larger scale;

FIGS. 8A-8B show the catheter of the present invention with the bellows member activation mechanism in the "closed" state (FIG. 8A) and in the "open" state (FIG. 8B);

FIGS. 9A-9B show the catheter of the present invention with the activation mechanism in the shape of the bellows member with the latch;

FIGS. 10A-10B show an alternative embodiment of the catheter of the present invention with threaded activation mechanism in the "closed" state (FIG. 10A) and in the "open" state (FIG. 10B);

FIG. 11 shows the threaded activation mechanism of the catheter of FIGS. 10A-10B on a larger scale;

FIGS. 12A and 12B show another embodiment of the catheter of the present invention with a squeezable sliding unit for controlling the "open" and "closed" states of the retaining mechanism, respectively;

FIG. 13 shows the squeezable sliding unit of the catheter shown in FIGS. 12A-12B;

FIGS. 14A and 14B show the modification of the catheter of the present invention with thumb slide based actuator in the "closed" and "open" states, respectively;

FIGS. 15A and 15B show the catheter of the present invention with a lever based actuator in the "closed" and "open" states, respectively;

FIGS. 17A and 17B show an alternative embodiment of the catheter of the present invention with the syringe based actuator with a locking mechanism in the "closed" and "open" states, respectively.

BRIEF DESCRIPTION OF THE PREFERRED EMBODIMENTS

Figure 2A:
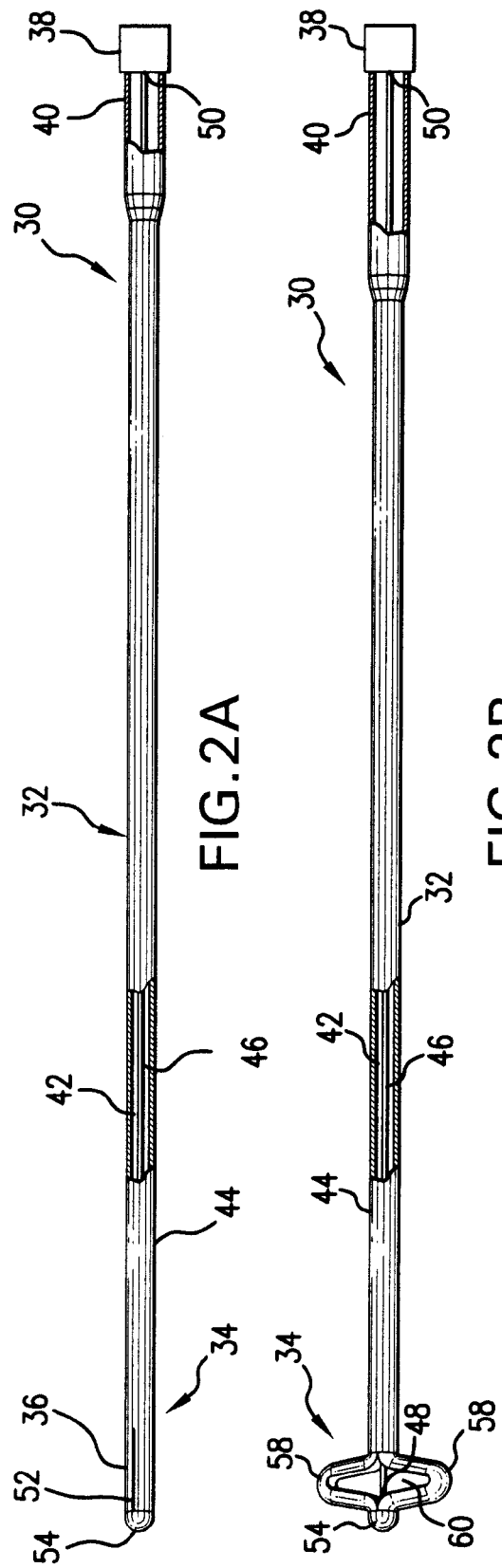
FIGS. 2A-2B is a schematic representation of the two-wings self-retaining mechanism of the catheter of the present invention in the "closed" and "open" states thereof, respectively.
Figure 2B:
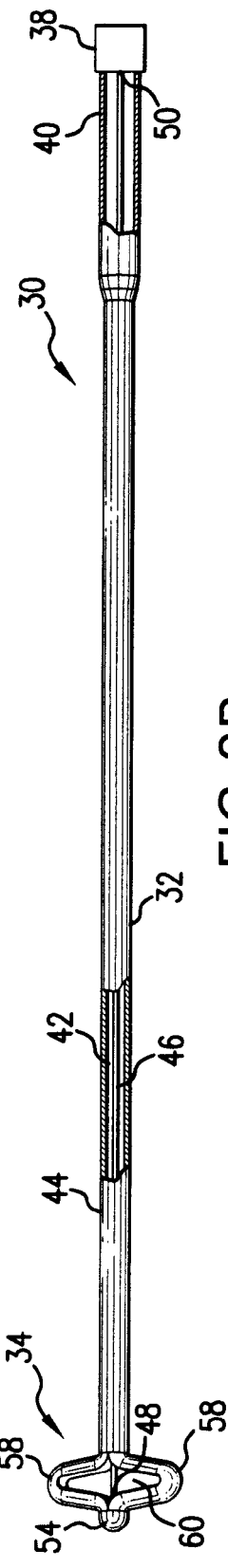
Figure 3A:
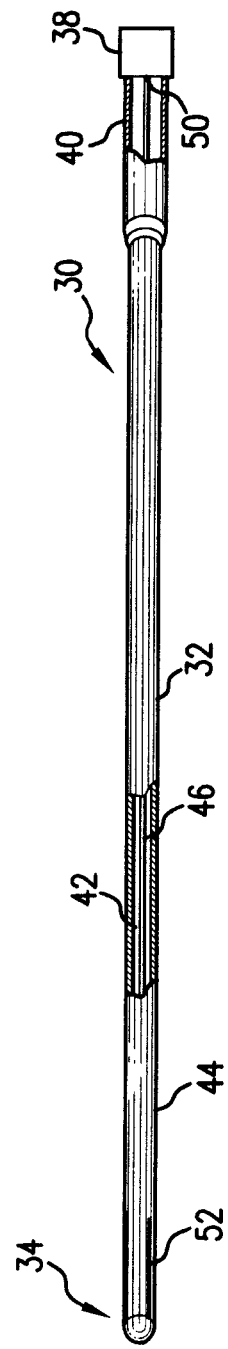
FIGS. 3A-3B is a schematic representation of the catheter of the present invention with a three wings retaining mechanism in its "closed" and "open" states, respectively.
Figure 3B:
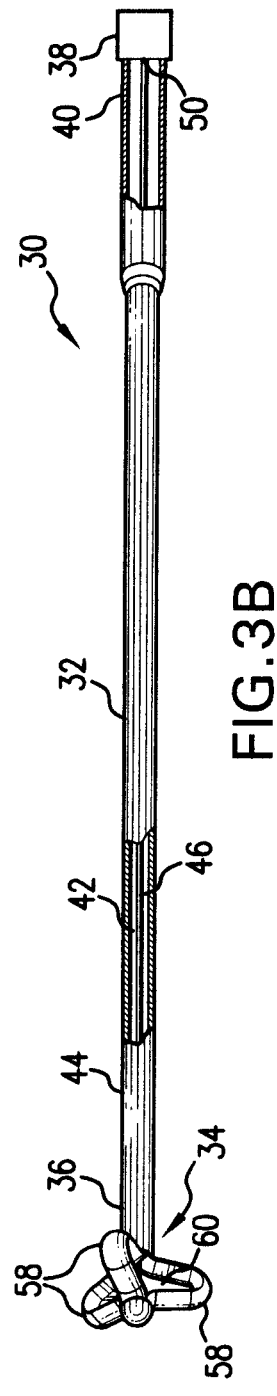

Referring to FIGS. 2A-5C, 8A-10B, 12A-12B, 14A-15B, and 17A-17B, the catheter 30 of the present invention includes a tubular member 32, a retaining mechanism 34 at the proximal end 36 thereof, and an activation mechanism 38 at the distal end 40 of the tubular member 32. A channel 42 is defined by the walls 44 of the tubular member 32 and extends between the proximal 36 and distal 40 ends thereof.

An actuation linkage 46 formed as a wire fabricated from plastic, Dacron, stainless steel, or nylon, is connected with the front end 48 thereof to the retaining mechanism 34 and with the tail end 50 to the activation mechanism 38 in order to transform the retaining mechanism between the "open" and "closed" thereof under the control of the activation mechanism 38 manipulated by a doctor or nurse or other medical personnel administering a procedure.

The catheter, in its "closed" state, is inserted into the urinary tract, and remains in place for some time, depending on the particular procedure. When the catheter is in the bladder, it may serve for drainage of urine or blood, administering of medication to the bladder, and/or irrigation of the bladder. For the purpose of retention in the bladder, the retaining mechanism 34 is transitioned into the "open" state which is achieved in different embodiments of the subject catheter in different ways as will be disclosed further herein. Once the procedure is completed, the catheter is removed if it does not need to remain there for a longer time period. For this, the retaining mechanism 34 is transitioned from the "open" state thereof into the "closed" state so that the medical personnel may easily remove the catheter from the bladder.

In the embodiment of the present catheter 30 shown in FIGS. 2A-3B, 8A-10B, 12A-12B, 14A-15B, and 17A-17B, the retaining mechanism 34 is designed with multiple slits 52, for example 2, 3 or 4 slits, extending at the proximal end 36 of the tubular member 32 in contact with the tip 54. Each slit 52 is cut at a predetermined position and has a predetermined length. In the "closed" state of the retaining mechanism 34, the slits are closed and the retaining mechanism occupies a minimal dimension possible for the design with no parts extending external the tubular member. This reduces discomfort when the catheter is inserted into or removed from the urinary tract of the patient.

When delivered into the bladder, which is seen by appearance of urine or blood at a drainage outlet 56 best shown in FIGS. 10A-10B, 12A-12B, 15A-15B, and 17A-17B, if the catheter is to be indwelled and retained in the bladder, the retaining mechanism 34 is transitioned into the "open" state thereof.

In the "open" state, the retaining mechanism 34 has its slits 52 opened so that the wings 58 are formed extending radially from the tubular member 32. The wings 58 have a span corresponding to the length of the slits 52. The wings 58 are separated by large openings 60 of a dimension sufficient to provide an effective drainage of the fluid (urine, blood) from the bladder to the drainage outlet 56 of the catheter with no residual urine in the urinary bladder.

The delivery of medicine or irrigation fluid into the bladder, when made through the multiple openings 60, provide complete contact of the medicine and irrigation fluid with the walls of the bladder in different directions thereby increasing the efficacy of the performed procedure. The tip 54 has a smooth surface which does not cause discomfort when it is in contact with the walls of the bladder. The wings 58 form a smooth curve between the tip 54 and the tubular member 32 at the lower end of the slits 52, and are flexible enough to avoid damage to the walls of the bladder when in contact therewith in the indwelling position of the catheter. As an additional benefit of the present design, even if there is an accidental opening of the wings while the retaining mechanism is in the urinary tract, and not in the bladder, the impact of the wings 58 on the walls of the urinary tract is so insignificant, that it does not cause damage to the urinary walls. The unintended opening of the wings of the catheter in question is highly improbable inside the walls of the urethra.

In order to transition the retaining mechanism 34 from the "closed" position (with slits 52 closed) into the "open" position (with the wings 58 extending radially from the tubular member), the actuation linkage 46, the front end 48 of which is connected to the tip 54, is retracted towards the distal end 40 of the catheter by the activation mechanism 38, as will be further described in following paragraphs. This action brings the tip 54 of the catheter closer to the lower end of the slits 52, thereby forming the wings 58 separated by the openings 60. The tail end 50 of the actuation linkage wire 46 is then fixed in position by the activation mechanism 38, to maintain the retaining mechanism 34 in the "open" state as necessary for the retention of the catheter in the bladder.

Although 2, 3, and 4 wing embodiments are presented in FIGS. 2A-3B and 14A-14B, it should be clear that any number of wings is possible subject to necessity and specifics of the urinary procedure.

Referring to FIGS. 4A-4C and 5A-5C, showing another embodiment of the catheter 30, the retaining mechanism 34 is formed with a plurality of leaves 62 which in the "closed" state of the retaining mechanism 34 are attached each to the other along the entire length thereof. When the retaining mechanism 34 is to be transitioned into the "open" state (in the indwelling position of the catheter), the leaves 62 are opened at the lower end 64 in the rotating motion actuated by a ∧-shaped memory block 66 to assume the "open" state in which the leaves 62 are angled each with respect to the other a predetermined angle.

For example, as shown in FIG. 4B, the ∧-shaped memory block 66 causes the opening of the leaves 62 into the intermediate position, and as shown in FIG. 4C, the ∧-shaped member block 66 forces the leaves 62 to open further and to assume a fully open position permitting the catheter to remain in the bladder for as long as needed.

There may be any number of leaves 62 in the retaining mechanism 34. For example, the design with two leaves is shown in FIGS. 4A-4C, and 6A-6B, and the design with or four leaves, is presented in FIGS. 5A-5D. The four-leaves design may have a spherical tip member 63 which is coupled to the front end 48 of the actuation linkage wire 46 and which is displaceable in the A-B directions therealong under the control of the activation member 38. When the catheter is in its "closed" state, shown in FIGS. 5A-5B, the spherical tip member 63 is at its most proximal position with the leaves 62 closed each to the other along the length thereof. However, when the catheter is to be transitioned into the "open" state, the actuation linkage wire 46 is retracted in the direction A by the activation mechanism 38, thereby "pulling" the spherical tip member 63 towards the distal end 40, and thereby opening the leaves 62, as shown in FIGS. 5C-5D. In the "open" state, the drainage openings 65, best shown in FIG. 5D, are formed sufficient for effective urinary procedures.

FIGS. 6A-6B show the diagonally open leaf arrangement of FIGS. 4A-4C in more detail. Each leaf 62 includes a portion formed of the material of the tubular member (such as, for example, silicone rubber) of a predetermined length connected at the lower end 64 thereof to the tubular member 32. Upper end 68 of each leaf 62 has a circular smooth surface in order to prevent urinary tract tissues from irritation when contact is made. A beam 70 is embedded into each leaf 62 along the length thereof, and the ∧-shaped memory block 66 is pivotally attached to each beam 70. The ∧-shaped memory block 66 has a pair of legs 72 coupled each to the other at the point 74 and to the beams by the ends 76.

The front end 48 of the actuation linkage wire 46 is connected to the upper point 74 of the ∧-shaped memory block 66. By reciprocating the actuating linkage wire 46 along the channel 42 of the tubular member 32, the upper point 74 of the ∧-shaped memory block 66 is displaced with regard to the point 64 at the foundation of the leaves 62, thereby changing the angle between the legs 72 of the ∧-shaped memory block 66. In this manner the change of the relative disposition between the legs 72 of the ∧-shaped memory block 66 is transformed into the angular displacement of the leaves 62 respective each other through the link which includes the legs 72 interconnected with the beams 70 embedded into the leaves 62.

When the actuation linkage wire 46 is retracted towards the distal end 40 of the catheter in the direction identified by arrow A, the leaves 62 assume a relative disposition with the angle therebetween at the point 64 while the sliding of the actuation linkage wire 46 towards the distal end 40 continues. Opposingly, when the actuation linkage wire 46 moves towards the proximal end 36 of the catheter in the direction identified by the arrow B, the angle between the leaves 62 is gradually decreased, thereby causing the closure of the leaves 62 each to the other. The ∧-shaped memory block 66 has the shape memory of the "closed" position. Once the wire 46 is released, the ∧-shaped memory block 66 will "close," thereby causing the leaves 62 to "close" each to the other with the slits therebetween.

The ∧-shaped memory block 66 has the shape memory, specifically of the angle between the legs 72 preferably corresponding to the "closed" state of the retaining mechanism 34. In this arrangement, when the actuation linkage 46 pulls the upper point 74 of the ∧-shaped memory block 66 in the A direction to the position corresponding to the "open" state of the retaining mechanism 34, the actuation linkage 46 has to be fixed at a specific position during the indwelling state of the catheter.

When the procedure is completed, the catheter is returned to the "closed" position in order for it to be removed from the urinary tract of the patient by releasing the tail end 50 of the actuation linkage wire 46 to permit the ∧-shaped memory block 66 to return to the initial "memorized" shape thereof, thereby "closing" the leaves 62.

Alternatively, the beams 70 may also constitute a part of the ∧-shaped memory block 66. Then the memory block 66 "memorizes" the overall shape and relative disposition of all the elements corresponding to the "closed" state of the catheter.

Shown in FIGS. 7A-17B, there are several types of the activation mechanism 38 contemplated for the catheter 30, each of which is applicable with each type of the retaining mechanism 34 described supra. Referring to FIGS. 7A-9B, the activation mechanism 38 includes a bellows member 75 having flexible corrugated walls 77 which is connected at the end 78 thereof to the distal end 40 of the tubular member 32. The bellows member 75 has another end 80 at the opposite edge to which the tail end 50 of the actuation linkage 46 is connected by a variety of mechanisms well known in the prior art. For example, the tail end 50 may be glued or soldered at the end 80 of the bellows member 74, or alternatively, may be secured in place with the help of a block 82 leaning against the corrugated walls 77. However other connections between the tail end 50 of the actuation linkage 46 and the bellows member 75 is contemplated within the scope of the present invention.

Figure 7A:
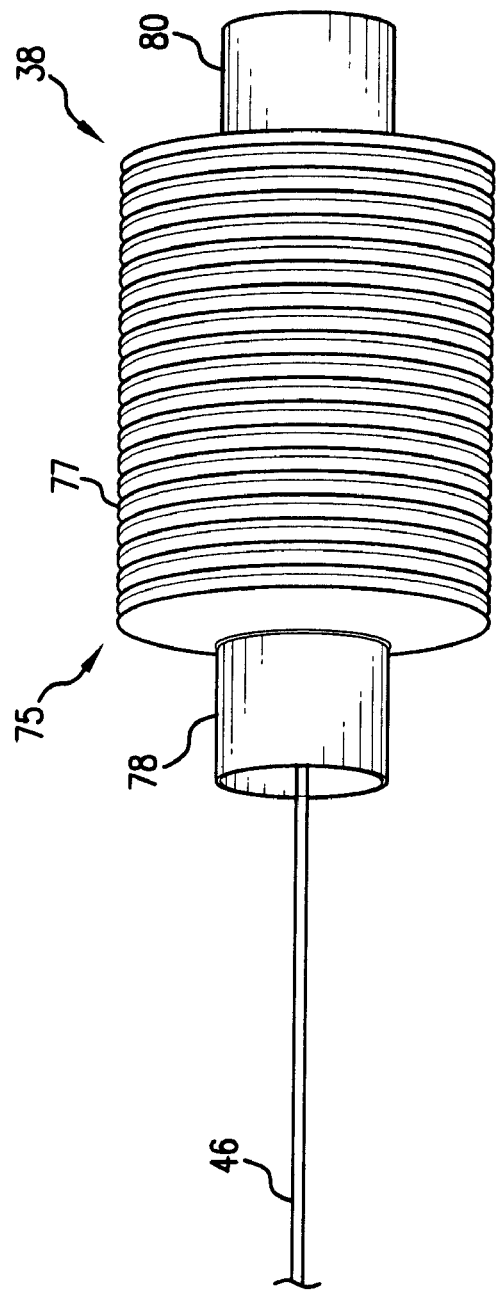
FIGS. 7A-7B show the activation mechanism in the form of the bellows member in a compressed state (FIG. 7A), and in an expanded state (FIG. 7B)
Figure 7B:
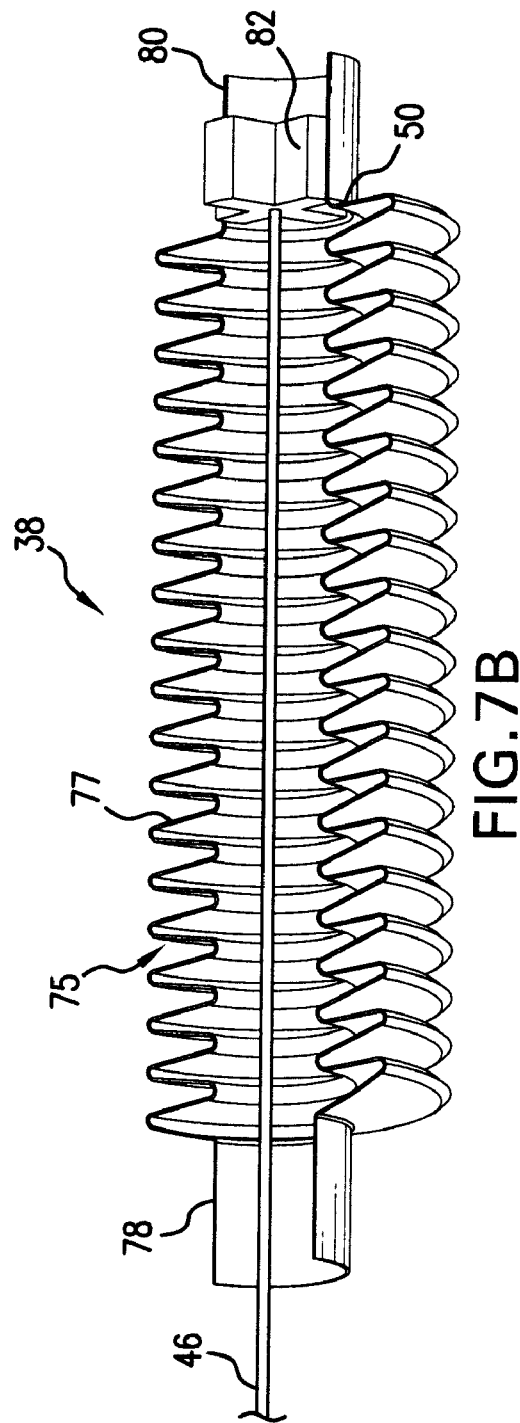

Due to the nature of its walls 77, the bellows member 75 is capable of changing the length thereof between a "compressed" state shown in FIG. 7A and "expanded" state shown in FIG. 7B. In the "expanded" state of the bellows member 75, the tail end 50 of the actuation linkage 46 is displaced towards the distal end 40 of the catheter 30. The front end 48 of the actuation linkage 46 is displaced therealong, thus causing the transitioning of the retaining mechanism 34 shown in FIGS. 2A into the "open" state, as was described in previous paragraphs.

There are several types of the bellows member 75 applicable in the subject catheter which permits alternative mechanisms of transitioning between the "compressed" and "expanded" states thereof. For example, the bellows member 74 may be a memory plastic bellows which may have the memory of "expanded" state, or "compressed" state, or both "expanded" and "compressed" state. Additionally, the bellows member may have no memory.

For example, in the embodiment where the bellows member 75 has a memory of the compressed ("closed") shape as well as the expanded ("open") state, the catheter, in its compressed state, is inserted into the bladder while having its retaining mechanism 34 in the "closed" state, as shown in FIG. 8A. The "compressed" state is insured during the introduction of the catheter into the urinary tract by the shape memory of the "compressed" state of the bellows member. The buttons 84 are held while manipulating the catheter. Once the catheter is in position, the medical personnel, still holding the buttons 84 by one hand, expands the bellows member 75 manually by the other hand into the "expanded" state to transition the retaining mechanism 34 into the "open" state, as shown in FIG. 8B. Once the bellows member 75 is expanded, it remains "open" since it has the "expanded" shape memory.

In order to transition the bellows into the "closed" (compressed) state when the catheter is to be removed from the urinary tract, with one hand on the buttons 84, the medical personnel pushes the end 80 of the bellows member 75 towards the buttons 84 for transitioning of the bellows member 75 into the "compressed" state, thereby closing the retaining member 34 and making the catheter ready for removal. Once the bellows member 75 is compressed, it remains compressed since it has the "compressed" shape memory.

When the bellows member 75 has only the "expanded" shape memory, in order for it to be compressed, as shown in FIG. 9A, a latch 86 is used to keep the bellows member 75 in its "compressed" state. When the catheter has been inserted into the urinary tract, it may be transitioned into the "open" state shown in FIG. 9B for retention in the bladder. For this, the medical personnel presses both resiliently biased buttons 84 each towards the other, thereby releasing the latch 86 which ceases to restrict the bellows member 75 to its "compressed" state. When the latch 86 is released, the bellows member 75 transitions into the "expanded" state thereof, and remains in such a state until the end of the procedure since it has the "expanded" shape memory. At the end of the procedure, when the catheter is to be removed from the urinary tract, the bellows member 75 is compressed manually until the opening 85 in the latch 86 engages with the button 84, as shown in FIG. 9A, in which position the bellows member 75 is maintained compressed for removal of the catheter from the urinary tract.

Referring to FIGS. 10A-10B and 11, showing another alternative embodiment of the present catheter 30, the activation mechanism 38 is formed with a pair of threadedly engaging members 88 and 90. As shown in FIG. 11, the tail end 50 of the actuating linkage 46 is coupled to the block 90. The rotation of the block 88 with respect to the block 90 causes a reciprocating motion of the block 90 with a corresponding displacement of the tail end 50 of the actuation linkage wire 46. This transfers into the motion of the front end 48 of the actuation linkage 46 with corresponding transitioning of the retaining mechanism 34 in "open" or in "close" states thereof.

Referring further to FIGS. 12A-12B and 13, in another alternative embodiment thereof, the activation mechanism 38 includes a squeezable block 92 which tightly embraces the tubular member 32. When squeezed, the squeezable block 92 releases the contact with the tubular member 32, and can slide along the tubular member 32 between the position corresponding to the "closed" state of the catheter shown in FIG. 12A, and the position corresponding to the "open" state shown in FIG. 12B.

As shown in FIG. 13, the squeezable member 92 has a ring 94 and a resilient cylinder 96 elastically encircling the tubular member 32. When the ring 94 is pushed towards the cylinder 96, the elastic connection between the cylinder 96 and the tubular member 32 is released, so that the entire arrangement may slide along the tubular member. The tail end 50 of the actuation linkage wire 46 attached to the squeezable member, moves therealong.

To actuate the activating mechanism 38 shown in FIGS. 12A-12B and 13, the personnel administering the urinary procedure inserts the catheter, in the "closed" state thereof shown in FIG. 12A, into the urinary tract and particularly into the bladder. A urine bag 98 is attached to the drainage outlet 56. The urine bag 98 is a bag with dimensions of approximately 10 inches×10 inches connected to a long tube (approximately 2 feet long). When urine or blood is seen in the urine bag 98 attached to the drainage outlet 56 of the catheter, the personnel squeezes and slides the squeezable block 92 towards the distal end as shown in FIG. 12B thereby retracting the actuating linkage wire 46 from the proximal end of the catheter, and thereby transitioning the retaining mechanism 34 into the "open" state thereof. When the "open" state is attained, the medical personnel "locks" the squeezable block 92 in position by releasing the ring 94 and leaves the block 92 at the position corresponding to the "open" state, shown in FIG. 12B.

Shown in FIGS. 14A-14B, is the four wing design with the actuator 38 with the thumb slide 100. In this modification, the catheter is transitioned into the "closed" state shown in FIG. 14A by moving the knob 102 along the slot 104 formed in the holder 106 attached at the distal end 40 of the tubular member 32 of the catheter by which action the tail end 50 of the actuation linkage 46 coupled operatively to the knob 102 is moved away from the distal end 40. To transition the retaining mechanism 34 into the "open" state in order to expand four wings radially from the tubular member, as shown in FIG.

14B, the knob 102 is moved by a thumb of medical personnel down the slide 104 closer to the distal end 40 of the catheter in one handed operation.

Figure 16A:
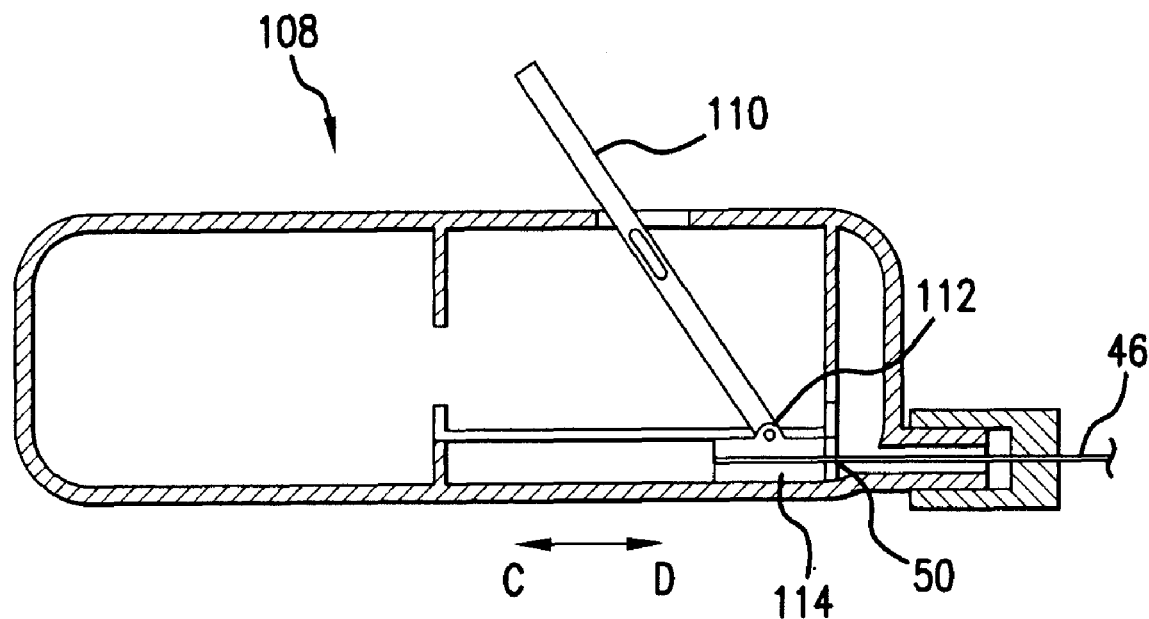
FIGS. 16A-16B show the lever based actuator of the catheter shown in FIGS. 15A-15B of the present invention.
Figure 16B:
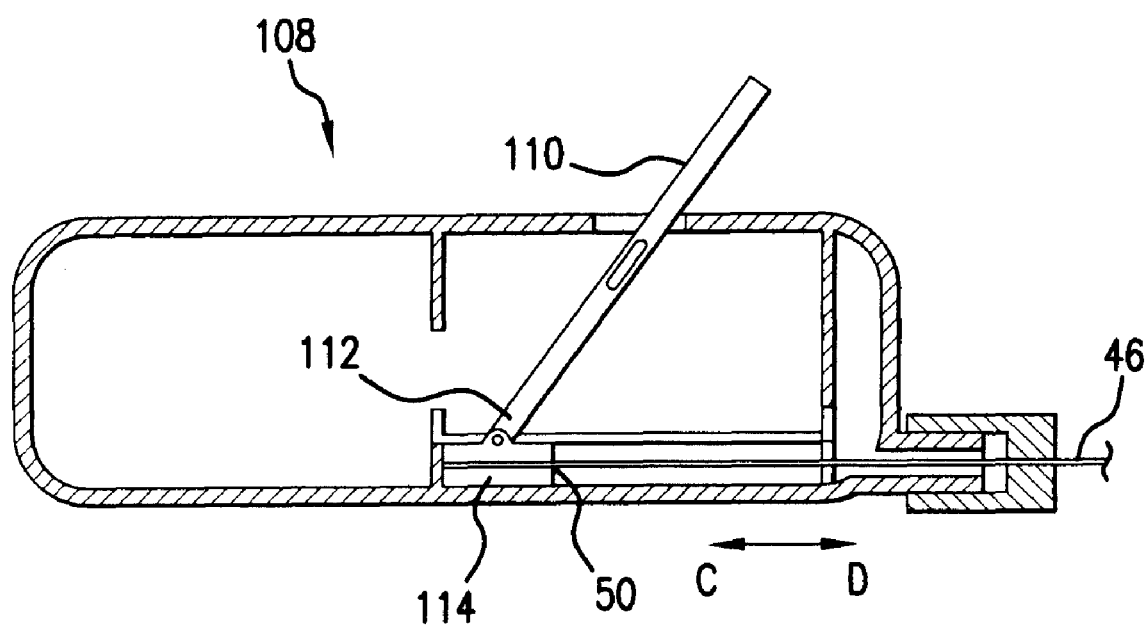

Shown in FIGS. 15A-15B and 16A-16B, a lever based actuator 108 is attached to the distal end 40 of the tubular member 32. The wire of the actuation linkage 46 can be pulled or pushed by manipulating the lever 110 as shown in FIGS. 16A-16B. The end 112 of the lever 110 is pivotally connected to the wire holder 114 which resiliently reciprocates in the direction identified by arrows C-D. By manipulating the lever 110, the wire holder 114 to which the tail end 50 of the actuation linkage wire 46 is attached, moves between the position shown in FIG. 16A corresponding to the "closed" state, and the position shown in FIG. 16B corresponding to the "open" state, dislocating the tail end 50 of the actuation linkage wire 46 accordingly and transitioning the retaining mechanism 34 between the "closed" and "open" states as needed.

As presented in FIGS. 17A-17B, the activation mechanism 38 in a further alternative embodiment is based on a syringe actuator 116 with the locking mechanism 124. The syringe based actuator 116 includes a hollow cylinder portion 118 attached to the distal end 40 of the tubular member 32 and a plunger portion 120 reciprocating within the hollow cylinder portion 118. The plunger portion 120 can be manipulated by the ring holder 122 or by any other arrangement. In the "closed" state shown in FIG. 17A, the plunger portion 120 is in its most advanced position within the hollow cylinder portion 118. In order to transition the retaining mechanism 34 into its "open" state when the catheter 30 is indwelled into the bladder, the medical personnel pulls the plunger 120 by the ring holder 122 in the direction E in the cylinder portion 118 so as to retract the tail end 50 of the actuation linkage wire 46 attached to the plunger 120 towards the distal end of the catheter, thereby causing the formation of the wings 58 at the proximal end of the tubular member 32 for retention in the bladder of the patient, as shown in FIG. 17B.

In the "closed" state, the relative disposition between the parts of the syringe based actuator 116 are locked through the locking unit 124 which may be of any design, as long as it provides a locking action between the counterparts. For example, the locking unit 124 may have a resiliently biased tooth 126 on the cylinder portion 118 releasably engageable with a slotted beam 128 on the shaft of the plunger. Alternatively, the locking mechanism may be devised with a resiliently biased hook member for engagement with a counterpart.

A Tuohy-Borst valve 130 may be installed at the connection between the distal end of the tubular member 32 and the syringe based actuator 116 to seal against fluid flow. Alternatively, a sealing material may be used in the channel actuating linkage lumen to prevent the ingress of urine to the syringe based actuator. Instead of, or in addition to the Tuohy-Borst valve, a ball seal may be used with a ball coupled to the tail end 50 of the actuation linkage wire 46, which reciprocates within the channel 42 at the distal end 40 thereof to close the channel when the catheter is indwelled.

The basic state of the subject catheter is the "close" state for added safety. The catheter may be transitioned into the "open" state only by intentional activation of the retaining mechanism 34 when the actuation linkage 46 is pulled toward the distal end 40 of the catheter. Even with a very low probability that the indwelling mechanism may be accidentally activated while the tip of the catheter is inside the urethra and not inside the urinary bladder cavity, the opening power of the retaining mechanism is not sufficient to overcome the strength of the urethral walls and to initiate the indwelling status. Therefore, the new catheter is safe in usage and avoids injury to the urethra.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of the elements may be reversed or interposed, all without departing from the spirit or scope of the invention as defined in the appended claims.

What is being claimed is:

1. A urinary catheter, comprising:
   (a) a tubular member having a proximal end and a distal end, said tubular member defining a longitudinal channel extending between said proximal and distal ends, adapted for passage of body fluids therethrough;
   (b) a retaining mechanism insertable in the urinary tract of a patient and positioned at said proximal end of said tubular member, said retaining mechanism being integrally and unitarily formed of a tubular flexible material controllably and selectively assuming an "open" position and a "closed" position;
   (c) an activation mechanism positioned at said distal end of said tubular member and being selectively reconfigurable between alternative fixed configurations wherein each configuration defines an open flow path through said urinary catheter and maintaining each of said fixed configurations devoid of a restraining force member, said activation mechanism being formed of a shape memory composition; for maintaining said activation mechanism in at least one of said selected configurations, and
   (d) an actuation linkage comprising a wire extending through said longitudinal channel of said tubular member and coupling said retaining and activation mechanisms each to the other, said actuation linkage reciprocally displaceable in said longitudinal channel bi-directionally relative to said tubular and retaining mechanism under control of said activation mechanism, thereby actuating said retaining mechanism to assume one of said "open" and "closed" positions thereof.

2. The urinary catheter of claim 1, wherein said actuation linkage is retracted towards said distal end to transform said retaining mechanism into said "open" state thereof.

3. The urinary catheter of claim 1, wherein said actuation linkage is selected from a group consisting of: stainless steel wire, Nylon wire, Dacron wire, and plastic wire.

4. The urinary catheter of claim 1, further comprising a drainage outlet coupled to said tubular member in fluid communication with said longitudinal channel thereof.

5. The urinary catheter of claim 1, wherein said retaining mechanism includes a tip at said proximal end and at least a pair of slits extending from said tip along walls of said tubular member at predetermined locations thereat, said actuation linkage being connected by one end thereof to said tip,
   wherein in said "open" state of said retaining mechanism, said tubular member forms at least a pair of elastic wings defined by said at least a pair of slits and spanning radially from said tip a distance corresponding to a length of each of said at least a pair of slits.

6. The urinary catheter of claim 1, wherein said activation mechanism includes a bellows member having a first end coupled to said distal end of said tubular member, a second end opposite to said first end, and flexible corrugated walls extending between said first and second ends of said bellows member,
   wherein a front end of said actuation linkage is connected to said retaining mechanism,
   wherein a tail end of said actuation linkage is connected to said second end of said bellows member, and
   wherein said bellows member is compressed to a compressed state to actuate said "closed" state of said retaining mechanism, and is expanded to an expanded shape to actuate said "open" state of said retaining mechanism.

7. The urinary catheter of claim 6, wherein said bellows member has a shape memory to memorize said expanded shape thereof.

8. The urinary catheter of claim 6, wherein said bellows member has a shape memory to memorize said compressed shape thereof.

9. The urinary catheter of claim 6, further including a latching member operatively coupled to said bellows member and actuated to transfer said bellows member between said compressed and expanded shapes thereof.

10. The urinary catheter of claim 9, further including a pair of projections operatively coupled between said latching member and said bellows member, said projections being actuated to control latching engagement between said latching and bellows members.

\* \* \* \* \*